(12) United States Patent
Foo

(10) Patent No.: US 8,781,563 B2
(45) Date of Patent: *Jul. 15, 2014

(54) ULTRA WIDEBAND MONITORING SYSTEMS AND ANTENNAS

(71) Applicant: Sensiotec Inc., Atlanta, GA (US)

(72) Inventor: Senglee Foo, North Vancouver (CA)

(73) Assignee: Sensiotec Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/851,287

(22) Filed: Mar. 27, 2013

(65) Prior Publication Data

US 2014/0070958 A1 Mar. 13, 2014

Related U.S. Application Data

(63) Continuation of application No. 12/281,146, filed as application No. PCT/CA2007/000365 on Mar. 6, 2007, now Pat. No. 8,428,696.

(60) Provisional application No. 60/778,908, filed on Mar. 6, 2006.

(51) Int. Cl.
| | |
|---|---|
| *A61B 5/04* | (2006.01) |
| *A61B 5/00* | (2006.01) |
| *H01Q 9/28* | (2006.01) |
| *G01S 13/56* | (2006.01) |
| *H01Q 21/06* | (2006.01) |
| *A61B 5/0205* | (2006.01) |
| *G01S 13/02* | (2006.01) |
| *A61B 5/103* | (2006.01) |
| *H01Q 21/00* | (2006.01) |
| *A61B 5/08* | (2006.01) |
| *G01S 7/00* | (2006.01) |
| *A61B 5/11* | (2006.01) |
| *G01S 13/88* | (2006.01) |
| *A61B 5/024* | (2006.01) |

(52) U.S. Cl.
CPC ............. *A61B 5/002* (2013.01); *A61B 5/742* (2013.01); *G01S 7/003* (2013.01); *A61B 5/1115* (2013.01); *G01S 13/886* (2013.01); *H01Q 9/285* (2013.01); *G01S 13/56* (2013.01); *A61B 2562/166* (2013.01); *A61B 5/6891* (2013.01); *A61B 5/6892* (2013.01); *H01Q 21/062* (2013.01); *A61B 5/024* (2013.01); *A61B 5/0205* (2013.01); *G01S 13/0209* (2013.01); *A61B 5/103* (2013.01); *A61B 5/02444* (2013.01); *H01Q 21/0075* (2013.01); *A61B 5/1117* (2013.01); *A61B 5/7207* (2013.01); *A61B 5/0816* (2013.01); *A61B 2562/046* (2013.01); *A61B 5/1113* (2013.01); *A61B 2562/0228* (2013.01); *Y10S 128/903* (2013.01)
USPC ................ 600/509; 607/30; 607/31; 607/32; 607/59; 607/60; 128/903

(58) Field of Classification Search
USPC ........................ 607/60, 30–32, 59; 128/903
See application file for complete search history.

(56) References Cited

U.S. PATENT DOCUMENTS

| | | | |
|---|---|---|---|
| 5,361,070 A | 11/1994 | McEwan | |
| 5,455,593 A | 10/1995 | Ross | |
| 5,861,019 A * | 1/1999 | Sun et al. | ......... 607/60 |
| 6,753,783 B2 * | 6/2004 | Friedman et al. | .......... 340/573.7 |
| 6,900,732 B2 | 5/2005 | Richards | |
| 6,919,838 B2 | 7/2005 | Santhoff | |
| 7,272,431 B2 * | 9/2007 | McGrath | ....... 600/509 |
| 7,304,580 B2 | 12/2007 | Sullivan et al. | |
| 2003/0090407 A1 | 5/2003 | Santhoff | |
| 2004/0100376 A1 | 5/2004 | Lye et al. | |
| 2004/0249258 A1 | 12/2004 | Tupin, Jr. et al. | |

FOREIGN PATENT DOCUMENTS

| | | |
|---|---|---|
| CN | 1700879 | 11/2005 |
| GB | 2349759 | 11/2000 |
| JP | 2001238922 | 9/2001 |
| WO | 9203090 | 3/1992 |

OTHER PUBLICATIONS

Enrico M. Staderini, UWB Radars in Medicine, IEEE Aerospace and Electronic Systems Magazine, IEEE Service Center, Piscataway, NJ, US, vol. 17, no. 1, Jan. 1, 2002, pp. 13-18.

Venkatesh, S., et al., Implementation and Analysis or Respiration-Rate Estimation Using Impulse-Based UWB, Military Communications Conference, 2005, Milcom 2005, IEEE Atlantic City, NJ, US, Oct. 17-20, 2005, Piscataway, NJ, US, pp. 1-7.

Chia, M.Y.W., et al., Through-Wall UWB Radar Operating Within FCC's Mask for Sensing Heart Beat and Breathing Rate, Radar Conference, 2005, EURAD 2005, European Oct. 6, 2005, Piscataway, NJ, US, IEEE, p. 283.

\* cited by examiner

*Primary Examiner* — Mallika D Fairchild

(74) *Attorney, Agent, or Firm* — Keusey & Associates, P.C.

(57) ABSTRACT

Apparatus for monitoring vital signs of one or more living subjects comprises a monitoring station and at least one sensor in communication with the monitoring station. The sensor comprises an antenna system, an ultra wideband radar system coupled to the antenna system, a signal processor and a communication system. The signal processor is connected to receive a signal from the ultra wideband radar system and configured to extract from the signal information about one or more vital signs of a person or animal in a sensing volume corresponding to the antenna system. The communication system is configured to transmit the information to the monitoring station.

32 Claims, 13 Drawing Sheets

ULTRA WIDEBAND MONITORING SYSTEMS AND ANTENNAS

CROSS-REFERENCE TO RELATED APPLICATIONS

This application is a continuation of U.S. application Ser. No. 12/281,146 which is a United States national phase entry of PCT application No. PCT/CA2007/000365 having an international filing date of 6 Mar. 2007 and claiming priority from U.S. application No. 60/778,908 filed on 6 Mar. 2006. U.S. application Ser. No. 12/281,146, PCT application No. PCT/CA2007/000365 and U.S. application No. 60/778,908 are all hereby incorporated herein by reference.

TECHNICAL FIELD

The invention relates to apparatus and methods for monitoring for the presence, activity and/or physiological signs of people or animals. The invention may be applied, for example, to monitor one or more of the presence, activity, heart rates and/or breathing rates of patients in a care facility. The invention also relates to antennas for transmitting and/or receiving electromagnetic signals.

BACKGROUND

Ultra wideband (UWB) electromagnetic signals can be used in a wide range of applications. Such signals typically comprise very short pulses presented at low duty cycles. As such, UWB signals can be advantageous, especially in applications in which it is desirable to maintain low average power levels. UWB radar can be used to measure the locations of objects at short ranges or to obtain images of objects. UWB devices can also be used for wireless communications, particularly for short-range and high rate data transmission.

UWB electromagnetic signals may have frequencies in the range of a few hundred MHz to about 12 GHz. In typical applications, UWB signals are used in the band from 3.1 GHz to 10.6 GHz. In particular UWB devices the frequencies of electromagnetic signals may be limited to particular regions of the spectrum to comply with applicable regulatory requirements. For example, some devices may be made to operate in a sub-band of the UWB spectrum that occupies the UWB spectrum in the range of 3.6 GHz to 4.6 GHz. In the United States this sub-band has been allocated by the Federal Communications Commission (FCC) for use by certain UWB devices.

While various UWB devices exist, there remains a need for practical and cost effective solutions for use in UWB systems. For example, there exists a need for practical and cost-effective antennas and antenna systems that can be used to transmit and/or receive UWB signals in various contexts. There is a particular need for such antennas that are compact and provide directional radiation patterns. There is also a need for practical and cost-effective UWB radar transceiver circuits.

Another field in which practical and cost-effective technology is required is the field of monitoring the vital signs of people or animals. For example, it would be beneficial to provide a system capable of monitoring the heart and breathing rates of patients in care facilities and in peoples' homes. While such systems exist, most have various disadvantages. For example, some require that electrodes or other devices be attached to each person being monitored, other systems are prohibitively expensive or insufficiently versatile, other systems are only capable of monitoring one vital sign, such as heart rate.

The prior art includes:

Newham, U.S. Pat. No. 5,471,198 and Edwards, U.S. Pat. No. 6,788,206 which disclose systems for monitoring for the presence of persons using reflected energy.

Richards et al., U.S. Pat. No. 6,900,732 which discloses a system for monitoring assets, objects, persons or animals using UWB signals.

Richards et al., U.S. Pat. No. 6,466,125 which discloses a system, electronic monitor and method that utilize impulse radio technology to alert medical personnel when a patient needs medical assistance.

Richards et al., U.S. Pat. No. 6,504,483 which discloses the use of impulse radio to track a position of a horse as it moves around a race track and/or to enable people to monitor one or more vital signs of the moving horse. The patent discloses that the technology may also work with other animals, such as dogs, and with people.

Hall et al., U.S. Pat. No. 6,661,342 which discloses the use of impulse radio to track moving athletes and to provide secure communication with athletes.

Nowogrodzki et al., U.S. Pat. No. 4,513,748 which discloses a heart rate monitor that utilizes two RF signals.

Bloice, U.S. Pat. No. 3,796,208 which discloses a system for monitoring movements of a patient using a microwave radar unit.

Lye et al, WO 2004/047630 which discloses a system that uses UWB signals to transmit information regarding the health condition of a user.

Tupin et al. U.S. 2004/0249258 which discloses the use of UWB radar for imaging and acquiring physiological data.

McEwan, U.S. Pat. No. 5,361,070, which discloses a UWB radar motion sensor.

Edwards, U.S. Pat. No. 6,788,206 discloses a patient monitoring system.

SUMMARY OF THE INVENTION

This invention provides apparatus and methods that relate to UWB systems. The apparatus and methods may be applied to systems for monitoring the vital signs of people or animals. The apparatus and methods also have other applications. Such methods and apparatus may incorporate various UWB technology as described herein. Systems according to some aspects of the invention may be implemented using continuous wave (CW) technology.

Some specific aspects of the invention provide antennas and antenna arrays that may be used to send and/or receive UWB signals; UWB radar transceiver circuits; and patient monitoring systems. These specific aspects of the invention may be applied independently of one another and may also be applied in various combinations.

Further aspects of the invention and features of specific embodiments of the invention are described below.

BRIEF DESCRIPTION OF THE DRAWINGS

In drawings which illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

The following description describes antennas for transmitting and/or receiving ultra wideband signals, circuits for generating ultra wideband signals and systems for monitoring for the presence, activity and/or vital signs of people or animals. The invention will be described with reference to a patient monitoring system that incorporates all of these elements. However, the various novel components and subsystems described herein also have application in other combinations and contexts.

Figure 1:
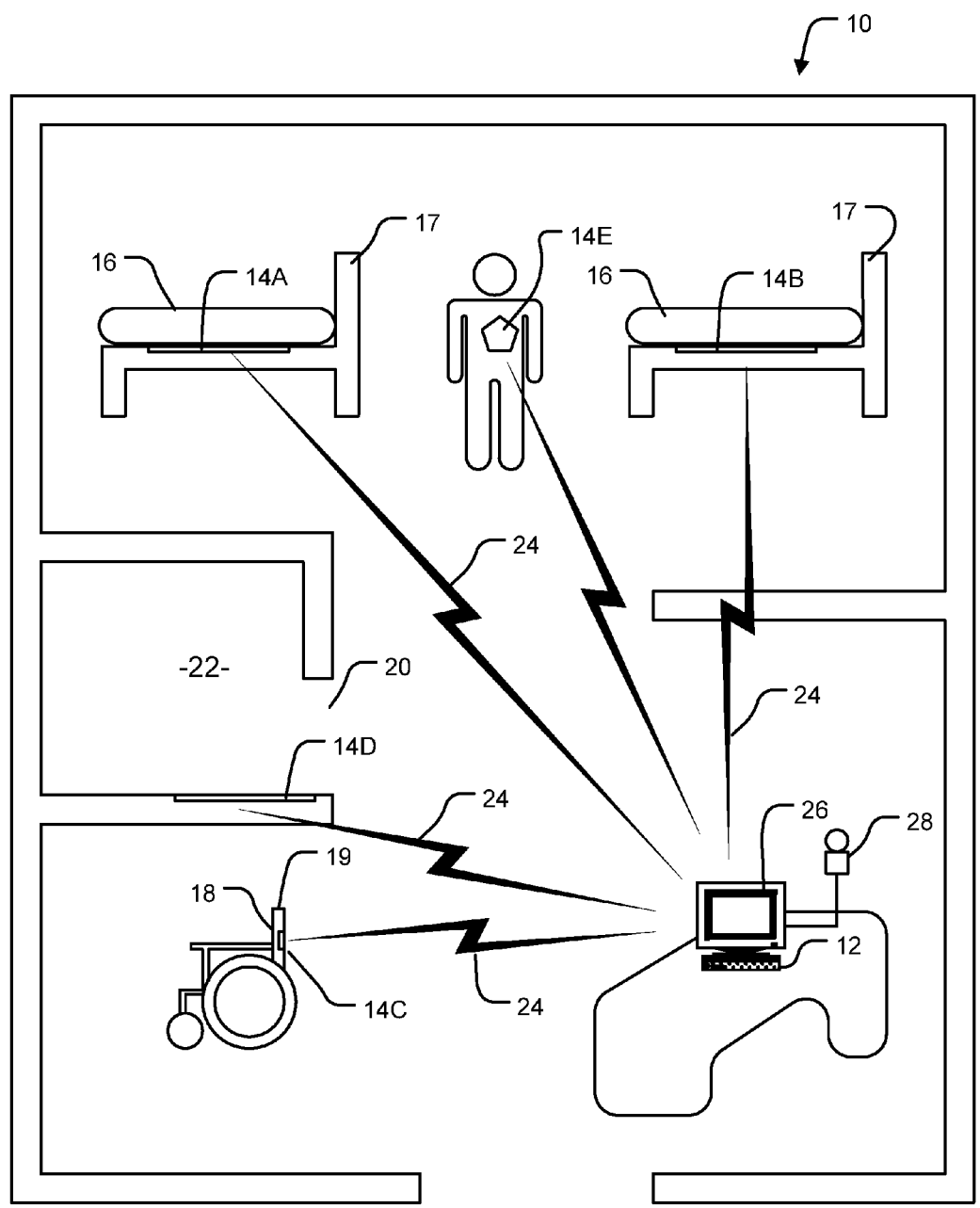
FIG. 1 is a block diagram of a patient monitoring system according to an embodiment of the invention.

FIG. 1 shows schematically a patient monitoring system 10. System 10 may be used, for example, in a hospital ward, a long term care facility, a nursery, or the like. System 10 has a monitoring station 12 and one or more sensing units 14. In the illustrated embodiment, sensing units 14 include sensing units 14A and 14B that are located under the mattresses 16 of beds 17, a sensing unit 14C that is built into (or mounted on) the backrest 18 of a wheelchair 19, a sensing unit 14D that is mounted at the entrance 20 of a restricted area 22 (restricted area 22 may be, for example, a dispensary in which medications are stored, an exit from the facility, or the like) and a sensing unit 14E that is strapped to a person's chest (as shown) or wrist (not shown).

Monitoring station 12 may receive signals from additional sensors (not shown) in addition to sensors 14. For example, monitoring station 12 may receive signals from door switches, proximity sensors, other patient monitoring devices such as EEG machines, blood oxygen sensors, or the like.

Each sensing unit 14 is in communication with monitoring station 12. The communication is preferably wireless communication. As described below, sensing units 14A, 14B, 14C and 14E monitor for the presence, activity and vital signs of a person at the location of the sensing unit 14. Sensing unit 14D is intended to detect the presence of personnel in restricted area 22. Sensing unit 14D may lack capabilities for detecting vital signs etc. Sensing units 14 may monitor one or more of:

a heart rate of the person;
a breathing rate of the person;
whether a person's breathing or heart beat has stopped;
whether a person's breathing or heart beat has an abnormal pattern;
whether or not the person is active (i.e. moving);
whether a person is moving in an unusual way (e.g. whether the person is moving in a manner that could indicate a seizure or fit)
whether or not a person is present in the vicinity of the sensing unit; and,
the like.

Data signals 24 that contain results from the monitoring operation are transmitted to monitoring station 12.

Monitoring station 12 comprises a display 26, a wired or wireless communication module 27 and an alarm 28 which may comprise, for example, a generator of alarm sounds. Communication module 27 receives data signals 24 from sensing units 14. Monitoring station 12 displays information regarding the various persons being monitored.

Figure 2:
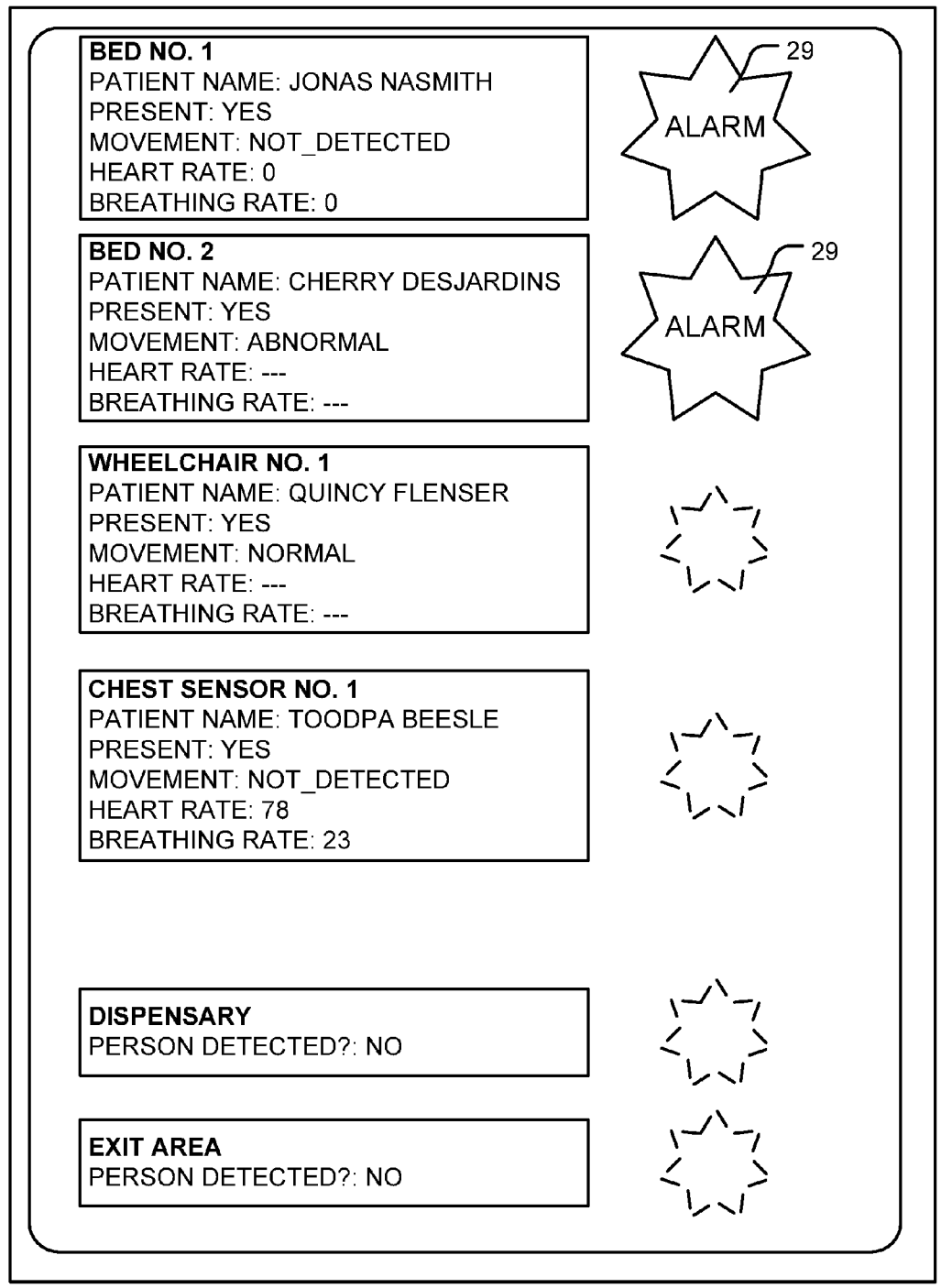
FIG. 2 is a schematic view showing a possible display for the patient monitoring system of FIG. 1.

FIG. 2 shows an example of a possible display. Monitoring station 12 may, for example, be located at a nursing station where it can be used by a duty nurse to monitor the status of patients. Monitoring station 12 may generate alarms if the data signals meet specified alarm criteria. The alarm criteria may include, for example:

a person is present but has not moved and has not had a detectable heart beat or respiration for more than a threshold period;
a person who should remain present at a sensing unit 14 is no longer detected as being present;
a person is detected in a restricted area; and,
the like.

An alarm may cause a visible indicia 29 to be displayed on display 26 (see FIG. 2) and may also or in the alternative cause an audible signal to be generated by alarm 28 which may comprise a buzzer or the like. A remote monitoring station (not shown) may be provided in addition to monitoring station 12. Monitoring station 12 is optionally in communication with a portable monitoring device such as a pager or the like that can signal to a responsible person when an alarm condition is detected at monitoring station 12.

Display 26 may display trends in a monitored person's motion as well as any vital signs being monitored as well as values for various vital signs being monitored by system 10.

Monitoring station 12 may be integrated with an overall patient management system that tracks patient information, treatment history, medication history and the like. Such systems are commercially available and are therefore not described further herein. Personnel at monitoring station 12 can observe the heart and respiration rates of patients being monitored and are warned by an alarm when a patient gets or falls out of bed, a patient stops breathing, a patient's heart stops, a patient is moving abnormally, or there exists some other condition or combination of conditions for which monitoring station 12 provides an alarm.

Figure 3:
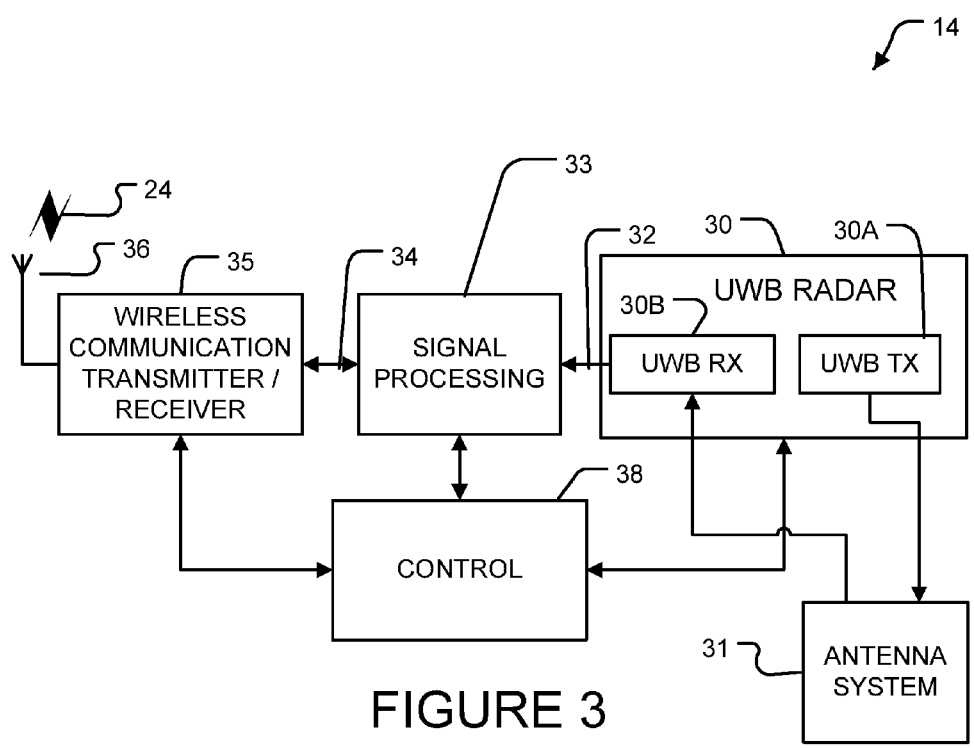
FIG. 3 is a block diagram of a sensing unit that could be used in the monitoring system of FIG. 1.

Sensing units 14 comprise ultra wideband (UWB) radar systems. FIG. 3 is a block diagram of an example sensing unit 14. Sensing unit 14 has a UWB radar system 30 connected to an antenna system 31. UWB radar system 30 has a UWB transmitter 30A, and a UWB receiver 30B. UWB radar system 30 generates UWB pulses that are transmitted by antenna system 31 into a space where a person may be located. This space may be called a "sensing volume" since UWB radar system 30 can be used to detect a person in the space. If a person is present in the space then the pulses are reflected at interfaces within the person's body, such as surfaces of the lungs and heart. Reflected pulses are received at antenna 31 and detected by UWB radar 30.

In some embodiments, the UWB pulses are in the C-band (3.6 to 4.6 GHz). The width of transmitted UWB pulses may be in the range of 1 ns to 3 ns, for example. UWB pulses are delivered at a suitable rate. The pulse rate may be set to a value low enough that the average emitted power is low enough to satisfy applicable regulatory requirements. For example, the pulse repetition interval (PRI) is in the range of 0.5 µs to 1 µs in some embodiments. The time-averaged transmitted output power may be relatively small. For example, the maximum effective isotropic radiation power (EIRP) may be −41.3 dBm/MHz or less.

A receiver output signal 32 from UWB radar system 30 is passed to a signal processing system 33. Signal processing system 33 processes receiver output signal 32 to obtain values for heart rate, breathing rate, and/or other characteristics being monitored by sensing unit 14. An output signal containing values for the characteristics is passed to wireless communication device 35 which transmits a signal 24 that carries data representing the values to monitoring station 12 by way of antenna 36. In the illustrated embodiment, a control 38 coordinates the operation of sensing unit 14. Control 38 may, for example, comprise a programmable microprocessor executing software instructions, logic circuits, or some combination thereof.

Figure 4:
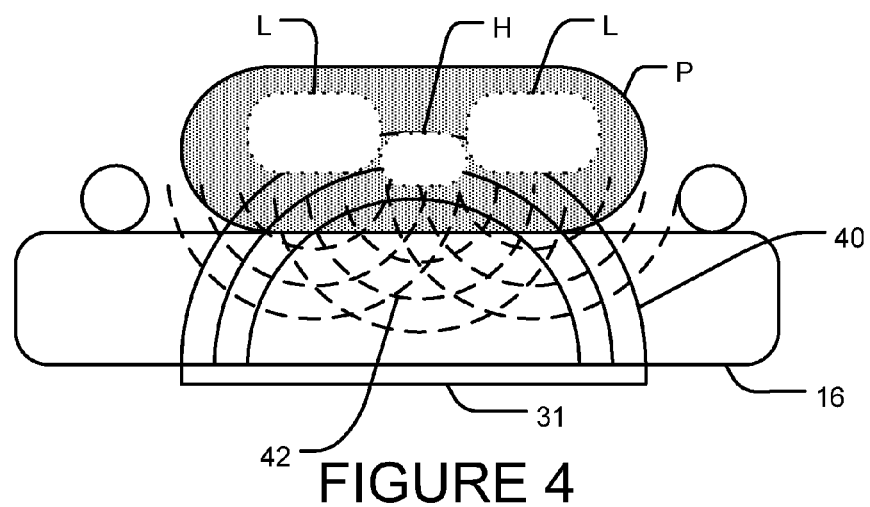
FIG. 4 is a schematic view showing a sensing unit detecting the presence of a person and the person's heart and respiration activity through a mattress by way of radiofrequency pulses.

FIG. 4 illustrates schematically how an antenna system 31 located under a mattress 17 can emit a UWB pulse 40. Pulse 40 passes into a person P and is reflected at various surfaces, including surfaces of the person's lungs L and heart H, to form reflected pulses 42 that are detected by antenna system 31. By using UWB radar in a back-scattering remote sensing mode, the system can monitor heart and respiration rates of a person without electrodes or other devices being attached to the body of the person.

Antenna system 31 may comprise an array of transmit antennas 31A and an array of receive antennas 31B. The transmit and receive antennas are distributed over an area broad enough to be able to cause and detect reflected pulses 42 from patient P in any reasonable position and posture on mattress 16. Transmit antennas 31A may be low-gain antennas. The use of low-gain transmit antennas 31A permits transmission of UWB signals having higher average amplitudes without causing EIRP to exceed thresholds that may be specified by applicable regulations. In some jurisdictions, regulations require that EIRP not exceed a specified threshold value. Further, since low-gain antennas generally have broad radiation patterns the radiation is distributed into a broad angular space.

Receive antennas 31B may be higher-gain antennas to provide better signal-to-noise ratios (SNR) for received signals containing reflected pulses 42.

Figure 4A:
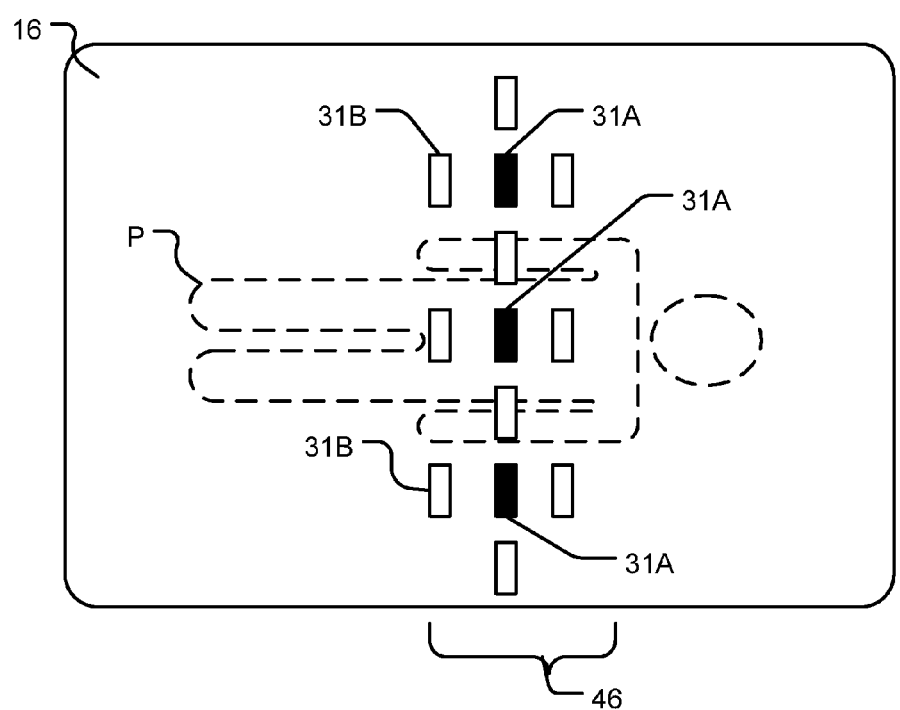
FIGS. 4A through 4C illustrate various alternative arrangements of antennas.

FIG. 4A shows an example arrangement of antenna arrays under mattress 16. A number of transmitting arrays 31A and receiving arrays 31B are arranged in a region 46 extending across mattress 16 at the expected level of the torso of a person P lying on mattress 16. Each transmitting array 31A is at the center of a cluster of receiving arrays 31B. In the illustrated embodiment, each transmitting array 31A is at the center of a group of four receiving arrays 31B that are approximately equally-spaced from a central transmitting array 31A. Arranging transmit antennas 31A and receive antennas 31B in an interleaved fashion facilitates obtaining a good signal-to-noise ratio. Transmit antennas 31A may be low-gain antennas that provide a relatively large coverage angle. This permits coverage of region 46 with relatively few transmit antennas 31A.

Figure 4B:
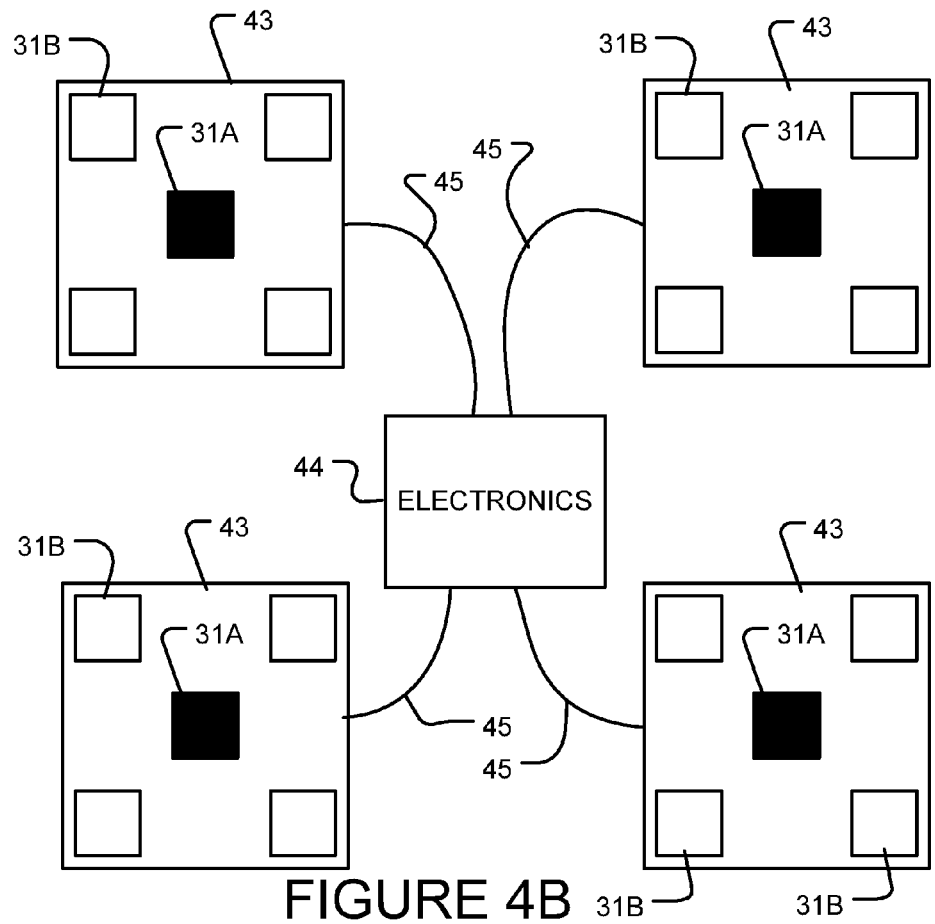

FIG. 4B shows another possible arrangement in which a number of antenna modules 43 each have a number of transmit antennas 31A and a number of receive antennas 31B. Modules 43 may be connected to an electronics module 44 containing a UWB transceiver by suitable waveguides such as coaxial cables 45. Each module 43 may be, for example, approximately 8 inches square. In the illustrated embodiment, each module 43 has four receiving antennas 31B and one transmitting antenna 31A. The antennas may be directly mounted or formed (for example by etching or printing) on a circuit board. Each module may optionally comprise a four-into-one power combiner to collect power from the receive antennas for delivery to electronics module 44.

The apparatus of FIG. 4B may be enclosed within a suitable housing for placement under the mattress of a bed. The housing provides insulation of antennas 31A and 31B from contact with any dielectric or metallic surface that could affect their performance. The housing may provide an air gap between antenna modules 43 and an underlying mounting surface. The housing may include a solid base plate to which the antenna modules and electronics module may be mounted. The base plate may, for example, comprise a sheet of aluminum or other suitable material. The housing may include a radome for environmental protection. The radome may be formed, for example, from a thin layer of plastic. A metallic shielding enclosure may be provided for electronics module 44.

Figure 4C:
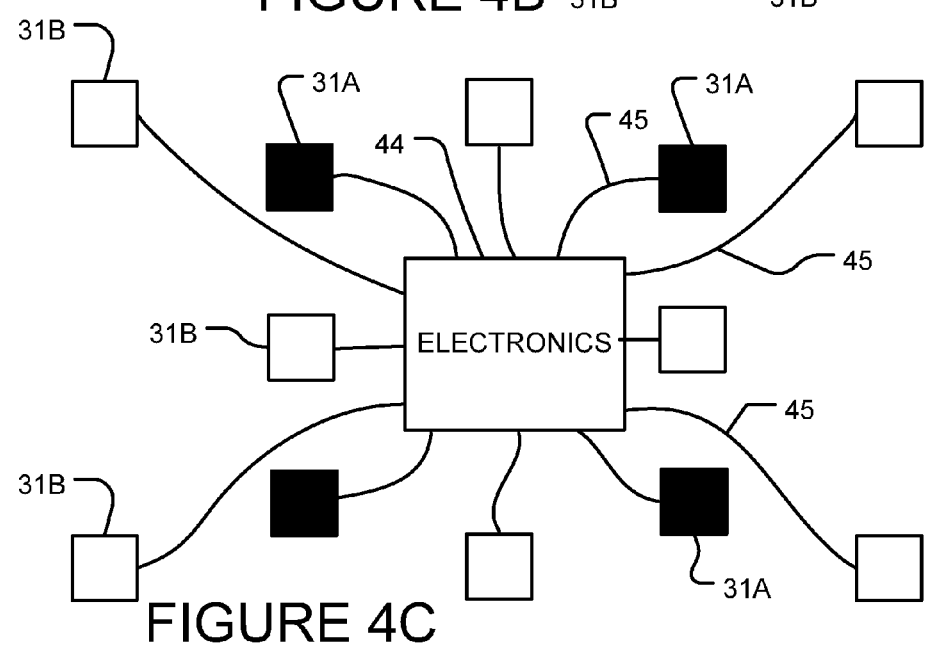

FIG. 4C shows another embodiment which has fewer antennas than the embodiment of FIG. 4B. Other arrangements of antennas are also possible.

Figure 5:
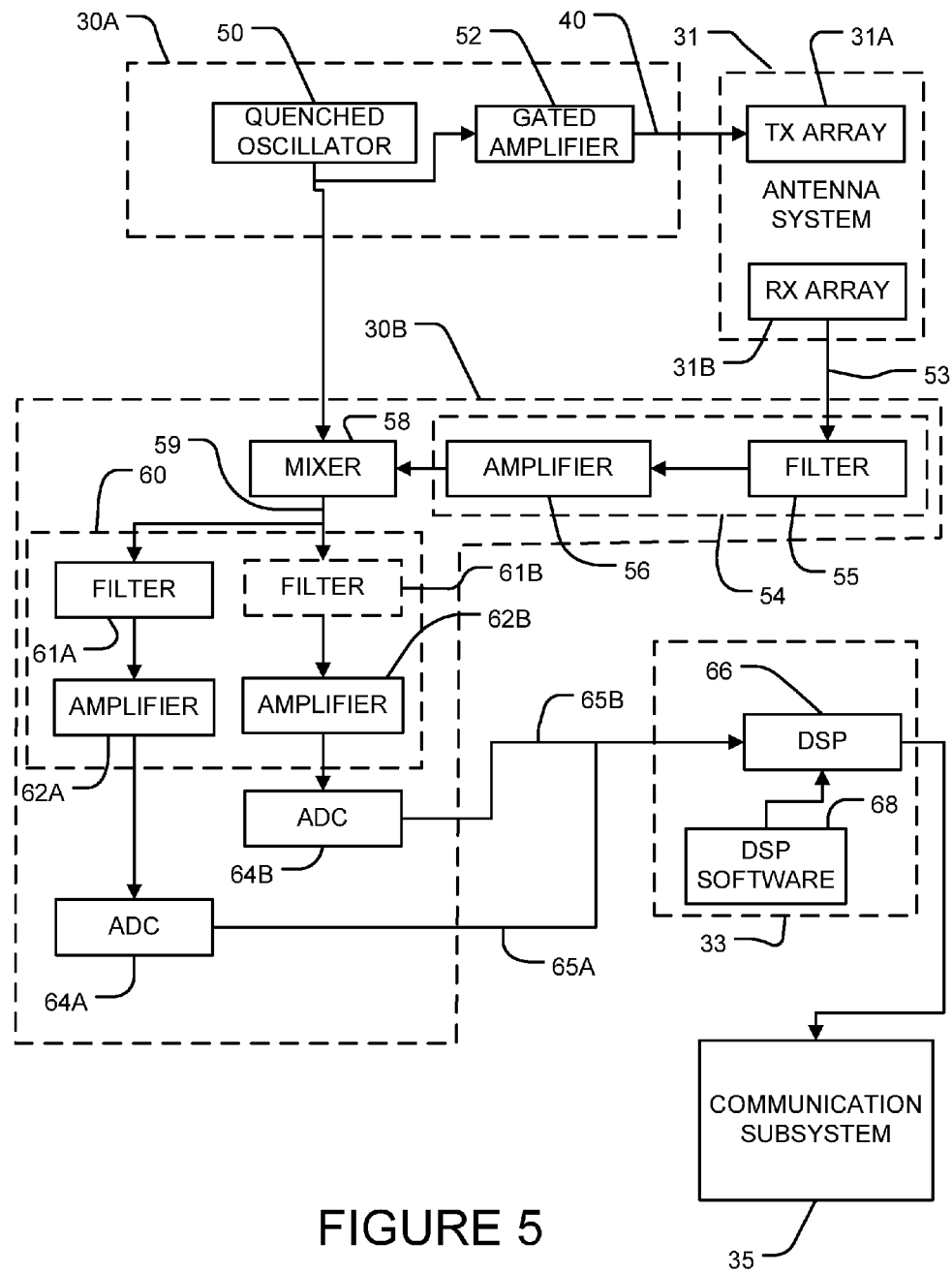
FIG. 5 is a block diagram of a sensing unit.

In an example embodiment illustrated in FIG. 5, UWB transmitter 30A comprises an oscillator 50 that is quenched to create a pulsed radiofrequency (RF) waveform that passes into a gated amplifier 52 to produce UWB pulses 40. It is generally desirable that the center frequency of oscillator 50 be tunable to allow for frequency optimization, if required. Any suitable oscillator circuit may be used in oscillator 50. A wide range of suitable oscillators are known to those skilled in the art. For example, oscillator 50 may comprise an oscillator based on a diode, FET or junction transistor.

In the example embodiment, UWB receiver 30B receives a signal 53 from receiving array 31B of antenna system 31 and passes the received signal through a RF signal conditioning stage 54 that comprises, for example, a filter 55 and an amplifier 56. The conditioned signal is provided to a mixer 58 where it mixes with a signal from oscillator 50 to yield a baseband signal 59. Baseband signal 59 is further conditioned in baseband conditioning stage 60, for example, by a filter 61 and amplifier 62. The conditioned baseband signal is then digitized by analog-to-digital converter (ADC) 64. ADC 64 is preferably at least a 12/14-bit ADC so that the conditioned baseband signal can be digitized with 80 dB in dynamic range. With an analog anti-aliasing filter of about 10 Hz, the sampling rate of the ADC does not need to exceed about 50 Hz to obtain a digitized signal from which heart rate and respiration rate can be extracted. To reduce the overall cost, size and power consumption of sensing unit 14, ADC 64 may comprise the ADC part of a combined ADC/microprocessor.

In currently preferred embodiments, a coherent Doppler detection scheme is applied to detect reflected pulses 42. The conditioned baseband signal has a frequency component that varies with a patient's heart beat and a frequency component that varies as the patient breathes. The conditioned baseband signal may be an audio frequency signal (for example, the conditioned baseband signal may have frequencies in the range of a fraction of a Hertz to a few Hertz).

In the illustrated embodiment, baseband conditioning stage 60 provides separate signal paths for conditioning respiration and heart-rate components of baseband signal 59.

This permits signal conditioning to be optimized for each signal component. FIG. 5 shows a filtering stage 61 comprising separate filters 61A and 61B, an amplification stage 62 comprising separate amplifiers 62A and 62B and a digitization stage 64 comprising separate analog to digital converters 64A and 64B that respectively condition a heart-rate signal 65A and a respiration-rate signal 65B.

The digitized signal 65 (having conditioned components 65A and 65B in the illustrated example) passes to signal processing stage 33. Signal processing stage 33 comprises a suitable data processor, such as a digital signal processor or microprocessor, for example, or suitable analog or digital signal processing circuits, such as a suitable configured field-programmable gate array (FPGA). In FIG. 5, signal processing stage 33 comprises a digital signal processor (DSP) 66 executing software instructions 68 stored in a program store accessible to DSP 66. DSP 66 extracts heart rate and respiration rate information from signal 65.

In some embodiments, DSP 66 is programmed to perform a transformation of the conditioned baseband signal into the frequency domain. An example of such a transformation is the Fourier transformation, which may be implemented as a fast Fourier transformation (FFT) algorithm. Heart beats in humans typically have frequencies in the range of 0.8 Hz to 3 Hz (50 to 180 beats per minute). Respiration in humans typically occurs at frequencies in the range of 0.1 Hz to 0.7 Hz (6 to 42 breaths per minute). DSP 66 can extract the patient's heart and breathing rates by searching in the transformed frequency domain signal for peaks at frequencies in the ranges expected for heart and respiration rates. The heart and respiration rate frequency ranges may be specified in DSP software 68 or stored in a data register accessible to DSP 66.

The heart and respiration rate ranges may be user-configurable. For example, infants may have heart rates that are substantially higher than the heart rates of adults. Where apparatus according to the invention will be used to monitor an infant, the heart and respiration rate frequency ranges may be set to higher values by way of a suitable user interface.

The accuracy of the results may be improved by performing the transformation into the frequency domain for relatively large blocks of data. For example, the transformation into the frequency domain may be performed by taking 3 or more blocks of conditioned baseband data at a time. Each block may contain, for example, 256, 521 or 1024 samples of the conditioned baseband data. Each time a new block is available, the transformation is repeated by dropping the oldest block and adding the newest block. The data on which each successive transformation is based therefore overlaps with the data for the immediately prior transformation. For example, where 4 blocks of data are taken at a time, there is a 75% overlap in the data used for each transformation.

Further enhancement may be made by using a previously-determined average heart rate to assist in identifying the heart rate signal in cases where there are multiple peaks in the frequency spectrum within the frequency-range corresponding to expected heart rates. In cases where DSP 66 identifies more than one peak in the frequency domain data that could be a heart rate, DSP 66 may be programmed to select the peak that is closest to the previously-determined average heart rate.

Harmonics of the respiration frequency can fall in the heart rate frequency range. Receiver 30B may be designed to minimize such harmonics. In some embodiments, DSP 66 may be programmed to detect frequency components that are harmonics of the heart rate or respiration rate and to determine the heart rate or respiration rate entirely, or in part from the frequencies of the harmonics. For example, the heart rate may be determined by detecting and measuring the frequency of the second harmonic of the heart rate and dividing the result by two.

In some cases, a person can have a respiration rate that is relatively high and a heart rate that is relatively low. In such cases, it may not be possible to separate the heart rate and respiration rate signals (especially because the signal level of the respiration rate signal is typically much larger than that of the heart rate signal—in some cases the respiration rate signal may be 20 dB to 30 dB higher in amplitude than the heart rate signal). This amplitude difference can be reduced somewhat by providing a filter that reduces the amplitude of the respiration signal in signal conditioning stage 60. For example, signal conditioning stage 60 may reduce the amplitude of signals in the respiration frequency range by 10 to 15 dB relative to signals in the heart rate frequency range.

Identification and measurement of the frequencies of respiration and heart beat signals may be enhanced by performing time-domain analysis of the conditioned baseband signal. For example, one can measure the respiration rate by counting peaks and zero-crossings in the conditioned baseband signal (which may be further conditioned by suitable filtering). By filtering out lower frequencies in the conditioned baseband signal one may also measure heart rate by counting peaks in the signal resulting from heart motion. Respiration rate information and/or heart rate information obtained by time domain analysis may be combined with corresponding information obtained by frequency domain analysis to obtain refined estimates of respiration rate and/or heart rate. In the alternative, respiration rate information and/or heart rate information may be obtained by time domain analysis instead of by frequency domain analysis.

In some embodiments, respiration rate and heart rate may be determined in two or more different ways and a value for the respiration rate or heart rate may be established by combining results obtained in the two or more different ways. For example, a system according to the invention may include a first means for determining the heart rate by directly identifying a frequency component corresponding to the heart rate in the Fourier transform of the conditioned baseband signal; a second means for determining the heart rate by identifying a frequency component corresponding to the second harmonic of the heart rate in the Fourier transform of the conditioned baseband signal; a third means for determining the heart rate by time-domain analysis of the conditioned baseband signal; and a combining means for combining results provided by the first, second and third means to yield a value for the heart rate. The combining means may, for example, take an average or a weighted average of the results.

DSP 66 averages the heart and respiration rates over suitable windows and provides updated averages to communication subsystem 35. For example, both the heart rate and respiration rate may be averaged over a window of 15 to 30 seconds. Since the respiration rate is typically less than the heart rate, respiration rate may optionally be averaged over a longer window. Shorter averaging times may be used initially to reduce the time between power up and the availability of heart rate and respiration rate information.

Heart rate and respiration rate are updated at a frequency which is sufficient to provide timely results. For example, heart rate may be updated every few seconds (e.g. every 1 to 5 seconds). If desired, respiration rate may be updated at a lower frequency (e.g. every 5 to 15 seconds).

When a patient moves, the motion causes large amplitude low-frequency components in the conditioned baseband signal. These low-frequency components can overwhelm the heart rate signal, the breathing rate signal, or both of these signals. For the duration of such motion it may be difficult to identify the heart rate signal or the breathing rate signal or both of these signals. DSP 66 is preferably programmed to detect such motion artifacts and to generate a signal (for example, by setting a motion-sensing flag) which indicates to monitoring station 12 that motion is detected and the motion is preventing the update of respiration rate and/or heart rate. DSP 66 may detect motion artifacts by identifying large amplitude low-frequency components in the conditioned baseband signal 65.

Communication subsystem 35 transmits the updated averages and any additional information, such as a motion flag, and an ID code that identifies the sensing unit 14 to monitoring station 12. Any suitable communication technologies and protocols may be provided to transmit data from sensing unit 14 to monitoring station 12. Some non-limiting examples are: a wired or wireless local area network (LAN) such as an ethernet LAN, an IEEE 802.11 network, or a wireless data communication system compliant with the ZigBee™ specification. Note that some processing may be performed at monitoring station 12 instead of at signal processing stage 33.

Heart rates do not typically change suddenly in comparison to the period of the heart rate. Monitoring station 12 (or DSP 66) may perform statistical analysis on the averaged heart rate and breathing rate values. For example, a new heart rate value may be compared to the previous average heart rate value. If the new heart rate value differs by more than a threshold amount (for example, 50%) from the previous average heart rate value then monitoring station 12 (or DSP 66) may be configured not to display the new value. In this situation, monitoring station 12 may indicate that the heart rate value is unreliable by displaying a symbol, instead of or in addition to the heart rate value, not displaying the heart rate value, displaying the heart rate value using different display parameters (e.g. flashing, a different color, etc.) or the like.

Monitoring station 12 may monitor heart rate and breathing rate signals for patterns that indicate a potential problem. For example, monitoring station 12 may be configured to trigger an alarm if a person's respiration rate suddenly increases and stays high, either on its own or in combination with other factors.

Figure 6:
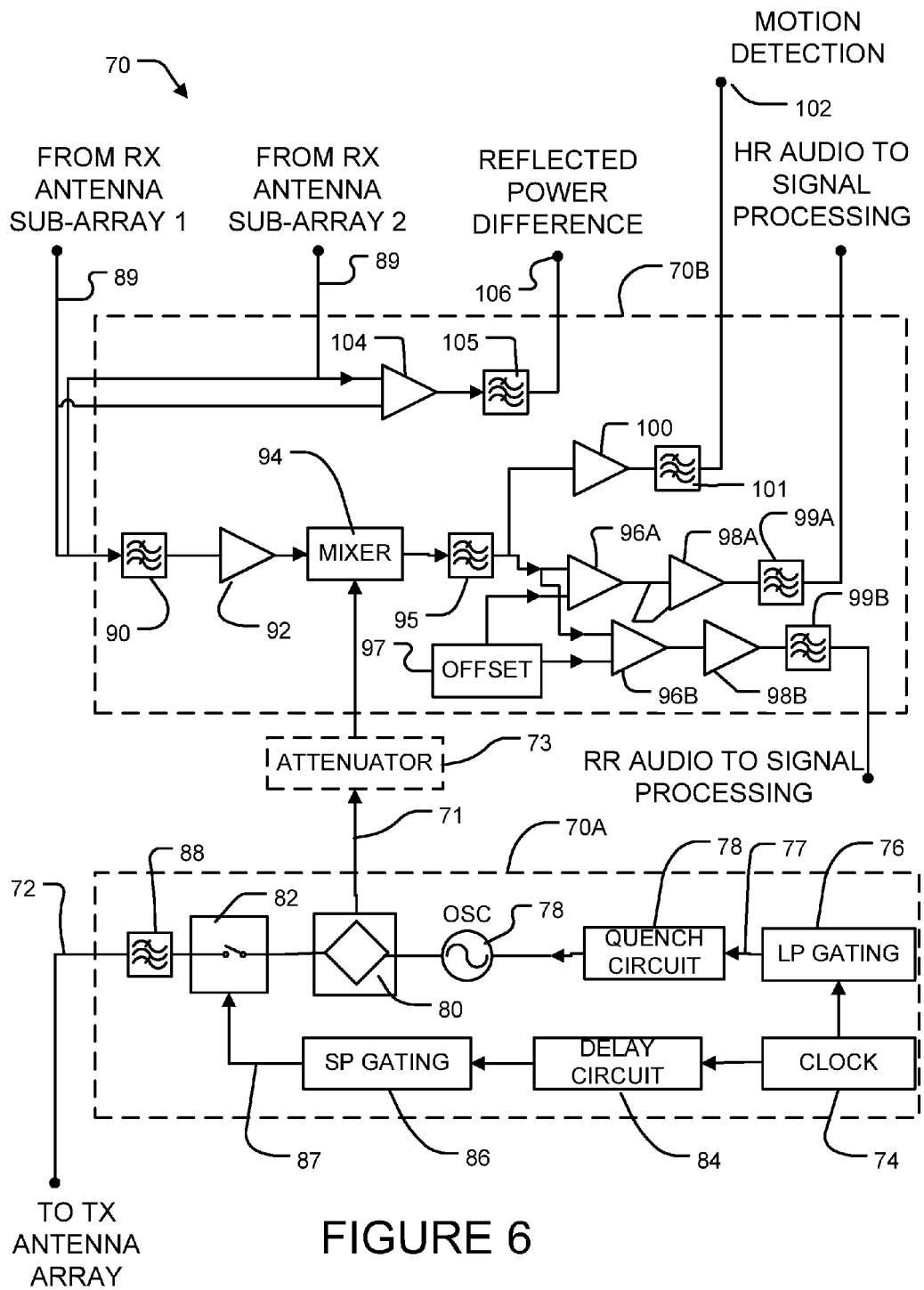
FIG. 6 is a block diagram of an RF radar transceiver that may be used in a sensing unit.

FIG. 6 shows a circuit 70 that may be used as UWB radar 30. Circuit 70 has a signal generation section 70A and a signal receiving section 70B. Signal generation section 70A produces a local oscillator signal 71 and a UWB pulse signal 72. Signals 71 and 72 have different waveforms. Signal 72 is made up of short UWB pulses having pulse-width of a few nanoseconds (ns).

Local oscillator signal 71 provides pulses that are longer than the pulses in signal 72 with the same carrier frequency as the pulses in signal 72. The length of pulses in local oscillator signal 71 should be sufficiently long to allow capture of all reflected pulses 42 in a range of interest. Reflected pulses 42 which arrive after the end of the local oscillator pulse will not be detected. It is desirable to keep pulses in local oscillator signal 71 short to exclude unwanted signals from the surroundings and to avoid unnecessary RF coupling. For example, the length of pulses in signal 71 is typically in the range of about 5 ns to 10 ns or so and may be adjustable. In some embodiments the pulses in signals 71 and 72 can be of the same or similar lengths.

In signal generation section 70A, a clock 74 operates to provide a clock signal at a desired pulse repetition frequency, for example, about 1 MHz to long-pulse gating circuit 76. Long-pulse gating circuit 76 generates pulses that cause quenching circuit 78 to quench oscillator 78 which operates at a suitable frequency (e.g. a C-band frequency). Local oscillator signal 71 is taken off at signal splitter 80.

After a time delay set by delay circuit 84, a short pulse is generated by SP gating circuit 86. The short pulse operates switch 82 to pass a very short RF pulse to the transmitting antenna array via filter 88. Keeping transmitted pulses short implies that the transmitted pulses will have a relatively broad bandwidth with low average signal level. Such low level signals can be made to meet regulatory requirements, such as requirements imposed by the Federal Communications Commission (FCC) in the United States which limit the allowable time-averaged and maximum signal levels. Delay 84 allows control over the relative timing between the transmit pulses in signal 72 and local oscillator signal 71.

Receiving section 70B receives a signal from a receiving antenna array. The signal is filtered at filter 90 and amplified by a low noise amplifier 92 before it is mixed with local oscillator signal 71 at mixer 94. An attenuator 73 may be provided to reduce the amplitude of local oscillator signal 71 upstream of mixer 94. A baseband signal output from mixer 94 is filtered at filter 95, adjusted for offset at differential amplifier 96A, amplified at amplifier 98A and filtered at filter 99A.

In the illustrated embodiment, differential amplifier 96A, amplifier 98A and filter 99A carry a signal from which heart-rate will be determined. A separate differential amplifier 96B, amplifier 98B and filter 99B are provided to condition a signal from which respiration rate will be determined. This facilitates separation of the heart-rate and respiration signals. The component of the demodulated signal at the output of mixer 94 that carries information regarding respiration is typically about 20 dB to 30 dB higher in magnitude than the component of the signal that represents heart rate. A high pass filter 99A in the heart rate channel can filter out much of the respiration signals. The high-pass filter may, for example, filter out signal components that have frequencies less than about 0.5 Hz and pass higher-frequency signals. Separation of the respiration signal from the heart-rate signal allows amplification of the respiration and heart rate signals to levels which facilitate time-domain signal processing of the signals.

Receiving section 70B provides separate outputs which carry signals from which reflected power and motion of a person can be detected. Motion detection output 102 receives a signal that is amplified by amplifier 100 and filtered by a high-pass filter 101. If the signal at motion detection output 102 has a value exceeding a threshold then this is an indication that the patient is moving enough to disrupt heart rate or breathing rate measurements.

Amplifier 104 and filter 105 respectively amplify and low-pass filter a signal taken at the output of mixer 94. This signal is presented at output 106. The amplitude of the signal at output 106 increases as the reflected power picked up by receive antennas 31B increases.

Reflected power may be measured by an envelope detector. The amplitude of reflected power will, in general, depend upon the configuration of the apparatus, the nature of the subject, the posture and location of the subject, and the like. In some embodiments, the presence or absence of a subject is determined by comparing reflected power received at two different sets of antennas (typically the two sets of antennas are two antenna arrays). The difference in the reflected power received at two arrays can be compared to a threshold to determine whether or not a subject is present. In such embodiments, amplifier 104 may comprise a difference amplifier, as shown in FIG. 6. An advantage of this construction is that it requires little or no adjustment to compensate for variability in the apparatus.

Where no person (or other person-like object) is present within the sensing volume then the signal at output 106 will have an amplitude within a given range. In the case of a bed sensor, this indicates that the bed is not occupied. In the case of sensors being used in other applications, this indicates that a person is not present within the sensing volume. When a person enters the sensing volume then the reflected power (or reflected power difference) indicated by the signal at output 106 changes. A system 10 may monitor the signal at output 106 and change a status flag from, for example, NOT_OCCUPIED to NORMAL when the signal at output 106 changes to a value outside of the range that it has when no person is present.

Circuit 70 may perform a calibration routine which sets the range of values corresponding to the bed being unoccupied when it is powered-up, or at other times when the bed is unoccupied in response to a user input.

A signal processing system 33 may set a status flag based on the combination of signals at outputs 102 and 106. The status flag may, for example, have values of NOT OCCUPIED, MOTION, and NORMAL. Some embodiments may have status flags for both normal motion and abnormal motion. The status flag indicating normal motion may be set when a person being monitored rolls over or changes position in a way that is normal and expected. The status flag indicating abnormal motion may be set when the person being monitored makes movements that indicate a possible problem that may require intervention. For example, the status flag indicating abnormal motion may be set when the person being monitored makes continued thrashing movements as may accompany certain types of seizure. Updating of heart rate and respiration rate values may be suppressed when the status flag has a value other than "NORMAL".

Figure 7:
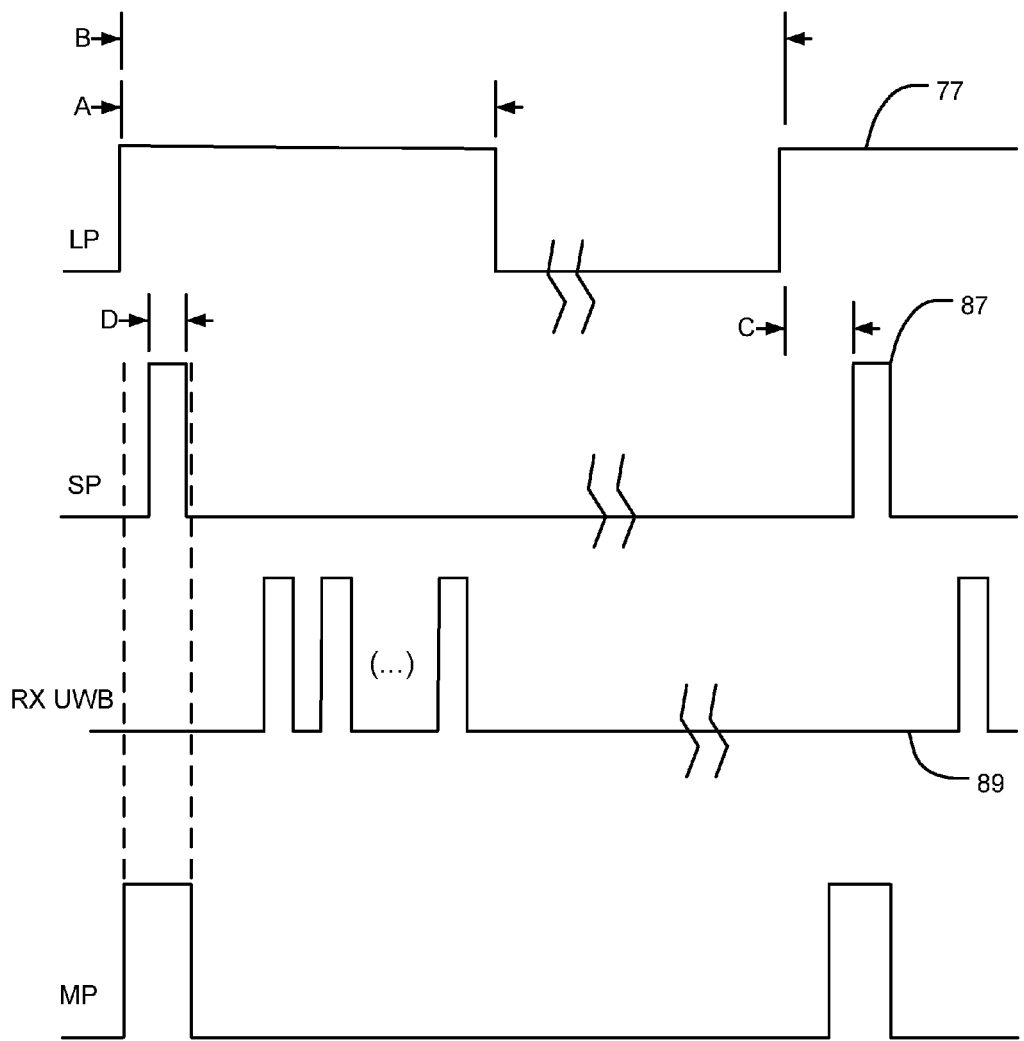
FIG. 7 is a timing diagram for parts of the radar transceiver of FIG. 6.

FIG. 7 is a timing diagram that illustrates the relative timing between shorter pulse gating signal 87 which controls the timing and lengths of transmitted UWB pulses in signal 72 and longer pulse signal 77 which controls the timing and duration of pulses in local oscillator signal 71. Signal 77 has pulses of length A, for example 5-10 ns separated by intervals of length B, for example, about 1 μs. In the illustrated embodiment, pulses in signal 87 begin at time C, typically a few ns, after the initiation of the longer pulse in signal 77. This promotes frequency and phase stability at the start of the oscillation. The pulses in signal 87 have lengths D, of a few ns (for example, 1-5 ns and preferably 3 ns or less, for example 1-2 ns). The pulse length D and pulse repetition rate may be chosen to achieve a time-averaged power density that is low enough to comply with limits imposed by applicable regulations.

Received signals 89 will arrive at receiver 70B in different time slots. The pulse length A during which local oscillator signal 71 is available is sufficiently long to encompass all received signals 89. The received signal is time gated at receiver 70B by the local oscillator signal. Using a local oscillator signal that is longer than the transmitted signal allows the simultaneous detection of signals from all receive antennas. As a result, channel multiplexing is not required. The local oscillator signal should not be unnecessarily long in order to prevent receiver 70B from receiving unwanted noise signals. In some embodiments, a blanking signal MP is generated at the start of each transmit pulse SP. Blanking signal MP is connected to suppress the reception of received signals 89 while UWB pulses are being transmitted. This prevents signals induced in the receive antennas by near-field coupling to the transmit antenna(s) from being mistaken for desired received signals 89.

The basic technology described above may be applied to systems that monitor a single person. For example, a sensing unit 14 may be provided to monitor for the presence, respiration rate and/or breathing rate of an infant in a crib or of a person in a bed or chair. An alarm may be integrated with sensing unit 14 or the sensing unit 14 may be connected to communicate an alarm signal to a remote alarm unit (either by way of a wired or wireless connection). In one embodiment, a sensing unit 14 is combined with a baby monitor. A base station of the baby monitor receives sounds made by an infant and also delivers an alarm signal in case the output from sensor 14 indicates a possible problem (such as the infant has stopped breathing). In another embodiment, a sensor 14 is connected directly to an alarm and operates the alarm if the sensor 14 detects that a person being monitored has stopped breathing for more than a short time. Such a system may be used with or without external monitoring to wake up a person who suffers from sleep apnea by triggering the alarm.

Figure 8:
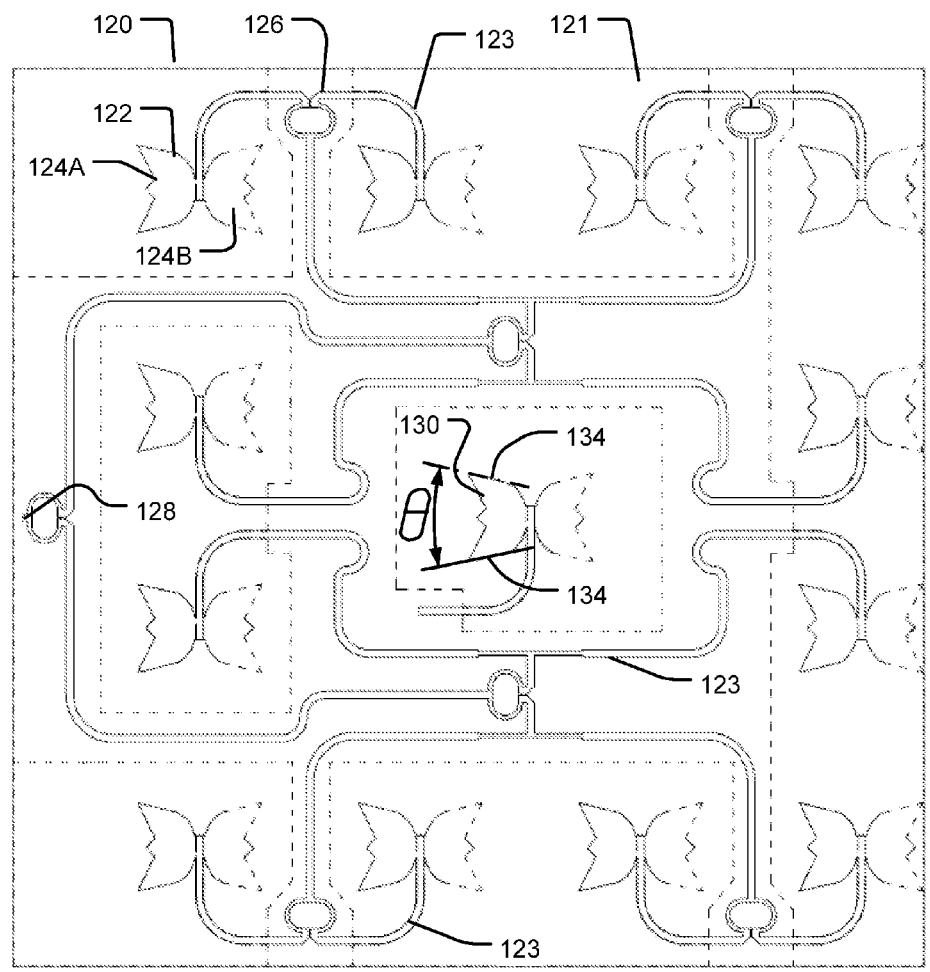
FIG. 8 is a plan view of an antenna array that may be used to transmit and receive UWB signals.
Figure 8A:
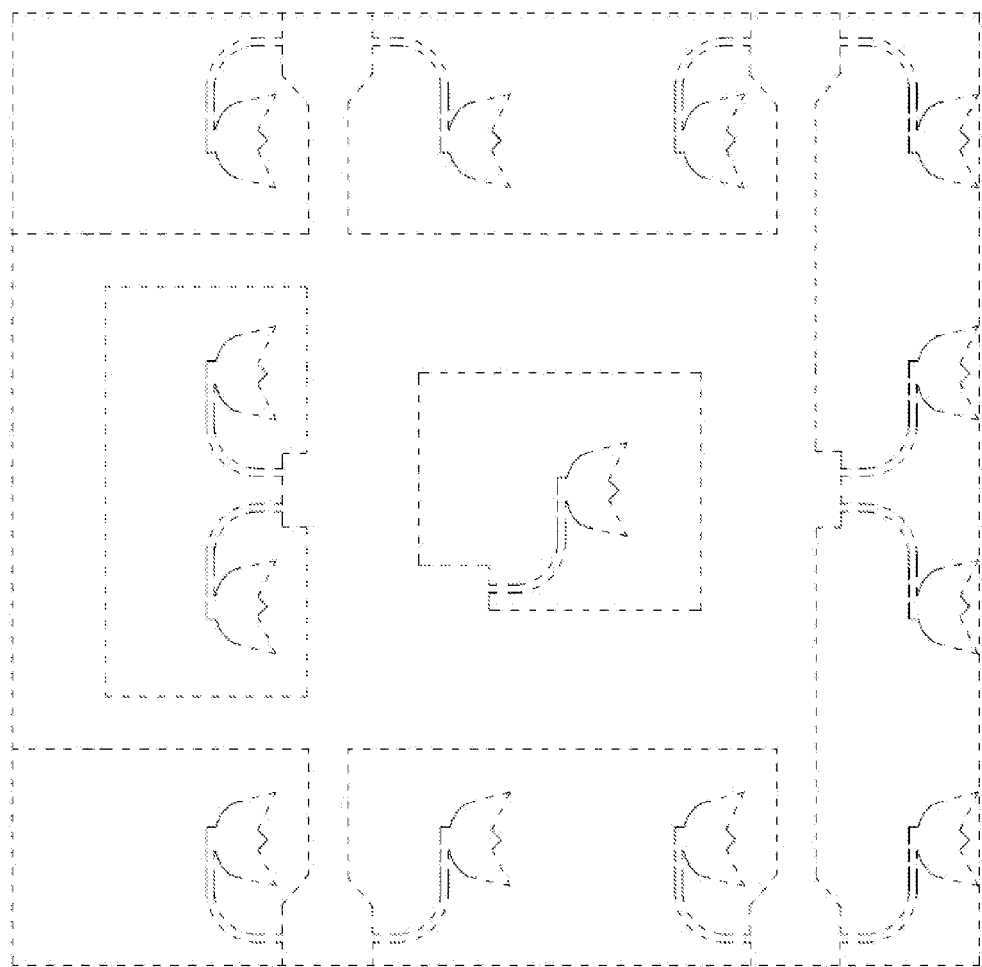
FIG. 8A is a plan view of the reverse side of the antenna array of FIG. 8.
Figure 8B:
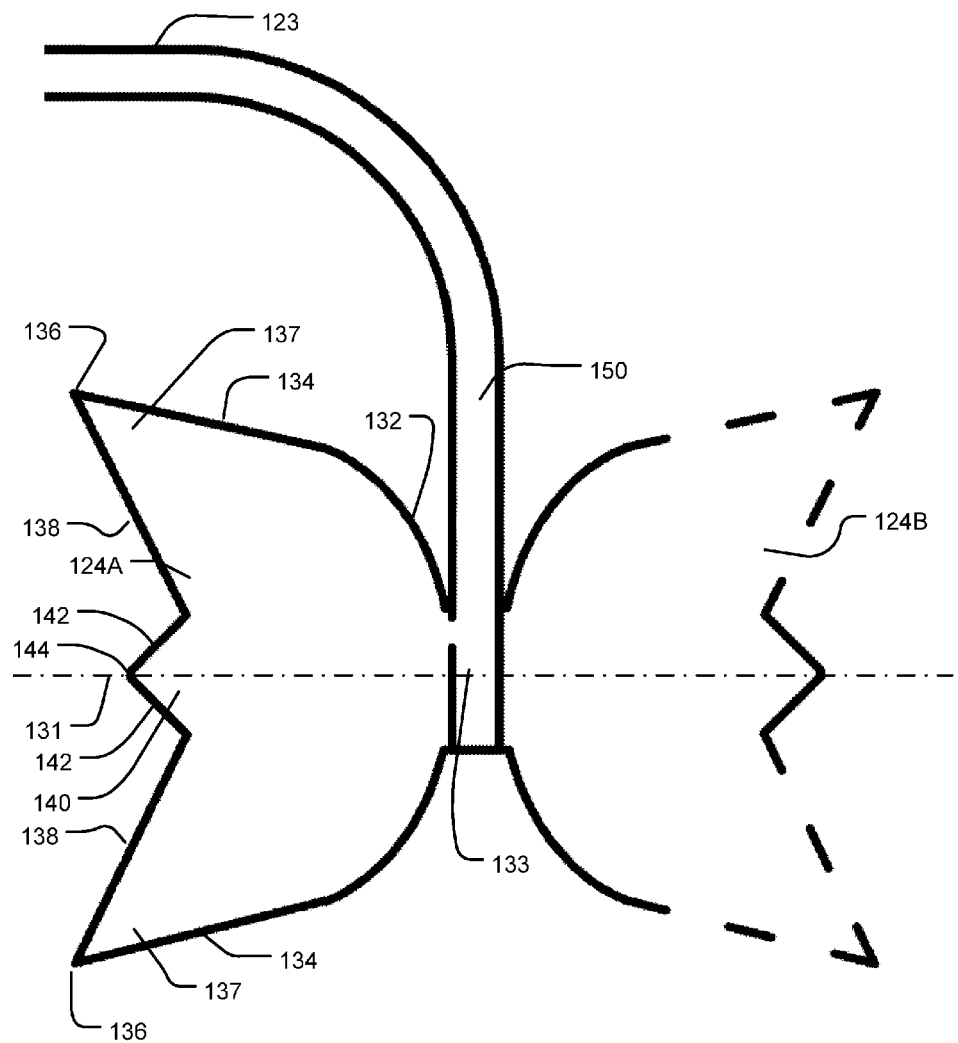
FIG. 8B is an enlarged view of an antenna element of the antenna array of FIG. 8; and, FIGS. 9, 9A, 9B and 9C are views of a compact antenna that may be used to transmit and/or receive UWB signals.

FIGS. 8, 8A and 8B show a design for an antenna array 120 that may be used in a system of the type described herein and may also be used for other applications. Individual antennas of the type shown in FIG. 8B may be combined into arrays of other types or used in stand-alone applications. Array 120 comprises a plurality of dipole-like antennas disposed on a planar substrate 121 such as a circuit board. Substrate 121 may comprise a two-sided copper-clad laminate in which the copper cladding has been patterned as shown in FIG. 8.

In FIG. 8, electrically conducting regions on a first side of substrate 121 are shown in solid outline while electrically conducting regions on a second side of substrate 121 are shown in dotted outline. FIG. 8A shows the pattern of electrically-conducting regions on the second side of substrate 121.

In the illustrated embodiment, twelve receive antennas 122 are interconnected by waveguides 123. Receive antennas 122 are located at nodes of a rectangular grid. Two-way signal combiners 126 combine signals from all of receive antennas 122 into a single output 128. A transmit antenna 130 is located in the centre of array 120. When array 120 is positioned at a proper height above a ground plane, both transmit antennas 120 and receive antennas 130 have directional radiation patterns.

Each antenna 122 and 130 has elements 124A and 124B that extend in opposite directions on opposite faces of substrate 121. A single antenna 122 is shown in detail in FIG. 8B. Elements 124A and 124B are mirror images of one another and are each symmetrical about a centre line 131. Each element 124A has a rounded segment 132 in the vicinity of its feed point 133 and a number of stubs of unequal length on its open end. In the illustrated embodiment, in each element 124, rounded segment 132 merges into straight diverging edge segments 134 which extend to corners 136 of outer stubs 137. The open end of the element 124 is W-shaped. Straight segments 138 form acute angles at corners 136. A central stub 140 is defined between substantially straight segments 142 which meet at a corner 144. In the illustrated embodiment, corner 144 is approximately a right angle.

The resonant frequencies of antenna 122 or 130 are determined primarily by the effective length of elements 124 in the Z-direction (i.e. in a direction parallel to line 131). Broad frequency bandwidth is achieved by providing a curved geometry near feed point 133 and multiple (three in the illustrated example) stubs of different lengths at the open end of the element. This geometry allows resonances at multiple frequencies due to its varying effective element length. In some embodiments, over 30% of frequency bandwidth can be achieved with or without use of a reflective ground plane.

The bandwidth of each antenna 122 or 130 can be adjusted by varying the subtended angle, θ (see FIG. 8) between segments 134. In general, the bandwidth increases as the subtended angle is increased and decreases as the subtended angle is decreased. By selecting an appropriate subtended angle θ in an antenna used to transmit a signal, the frequency spectrum of transmitted radiation can be adjusted. By selecting an appropriate subtended angle θ in an antenna used to detect signals, unwanted signals may be filtered from the received signal.

The input impedance of radiating elements 124 is matched to a 50 ohm unbalanced microstrip transmission line 123 through a pair of balanced strip lines 150 of constant width. By selecting an appropriate length for balanced strip line 150 and by selecting appropriate dimensions for the feed point 133 of the antenna 122 or 130, the antenna 122 or 130 can be matched to a 50 ohm unbalanced transmission line without any additional matching network.

Antenna array 120 has the advantages that can be made with standard circuit board manufacturing techniques and provides a compact balanced dipole structure suitable for transmitting and receiving UWB pulses.

As noted above, UWB radar may be used to detect the presence, movement, heart and respiration rates of a person sitting in a chair. A sensing unit for use on a chair back, as a sensor to be strapped-onto a person's chest or back, as a sensor to be used in conjunction with a baby crib, or in similar applications does not need to cover a field as large as a sensing unit for use in a full-sized bed. Consequently, a sensing unit for such an application may be made to have fewer antennas than would be required to cover a full-sized bed. For example, a sensing unit for sensing the presence, heart rate, and/or respiration rate of an infant in a small crib does not need to cover a large field and may have only one antenna or just a few antennas.

FIGS. 9, 9A, 9B and 9C show a compact antenna 170. Antenna 170 comprises a radiating element 172 that can be mounted directly to a circuit board, for example, by soldering, attachment using an electrically-conductive adhesive, or the like. Antenna 170 may be used in a sensing unit as described herein or may be used in other applications.

Antenna 170 has a three-dimensional configuration. Radiating element 172 is mounted above an electrically-conducting ground plane 174. Ground plane 174 may comprise a layer of metal on a printed circuit board substrate, for example. Radiating element 172 may be formed by stamping a thin metal sheet, for example.

In some embodiments, an electronics module containing UWB radar comprises a circuit board to which a radiating element 172 can be attached to provide an antenna 170. The circuit board may also comprise locations to which waveguides can connect external antennas or antenna arrays. Depending upon the application, a radiating element 172 or one or more external antennas or antenna arrays may be connected to the circuit board. This permits the same circuit board to be used in sensing units of various types. For example, a number of antenna arrays can be connected to the circuit board for use as an in-bed sensor while a radiating element 172 can be connected to the circuit board for use as a sensor in a chair back, under the mattress of a baby crib, or the like.

Antenna 170 radiates linearly polarized E-fields through the narrow gaps 178 between the radiating element and the ground plane 174. The resonant frequencies of the antenna are primarily determined by the overall dimensions of antenna 170 in the X and Z directions. A small stub 180 extended above the open end 182 of radiating element 172 can be provided to fine tune the resonant frequencies of antenna 170. The characteristics of antenna 170 may also be altered by providing a dielectric material between radiating element 172 and ground plane 174.

The geometry and dimension of antenna 170 in the Y direction determines the frequency bandwidth of antenna 170. Triangular shapes 184 of the geometry at both sides of antenna 170 allow for broadband frequency of operation. Over 20% of frequency bandwidth can be achieved with a proper shaping. Some embodiments of antenna 170 have a cardioid radiation pattern with directivity between 6 dBi to 8 dBi, depending on the size of ground plane 174.

An input feed point 188 is recessed into antenna 170. By selecting an appropriate distance of feed point 188 from edge 190, antenna 170 can be directly matched to a 50 ohm transmission line without an additional matching network.

For UWB operation, antenna 170 may have a radiating gap 178 of about 1 mm and a distance between the top of the radiating element 172 and ground plane 174 in the range of about 5 mm to 6 mm.

Figure 9:
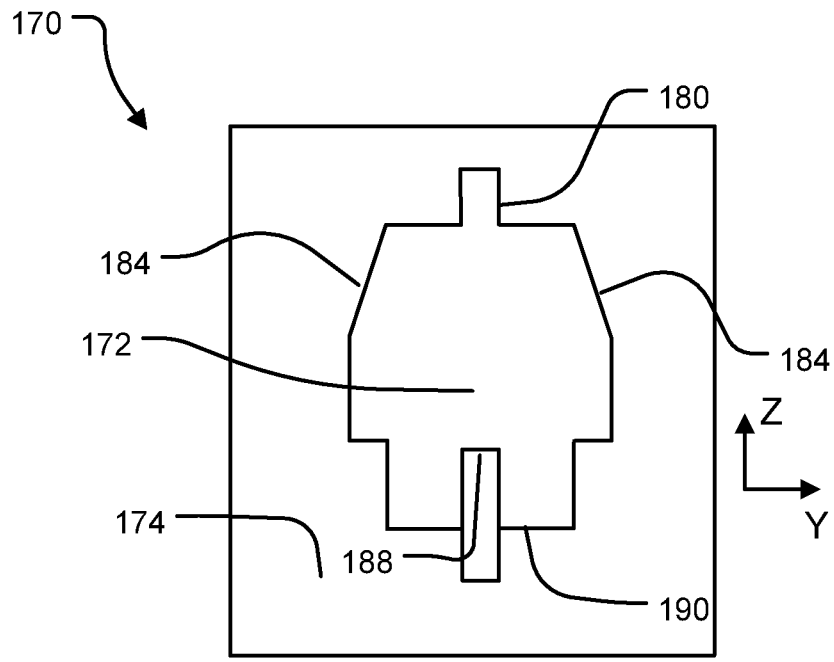
Figure 9A:
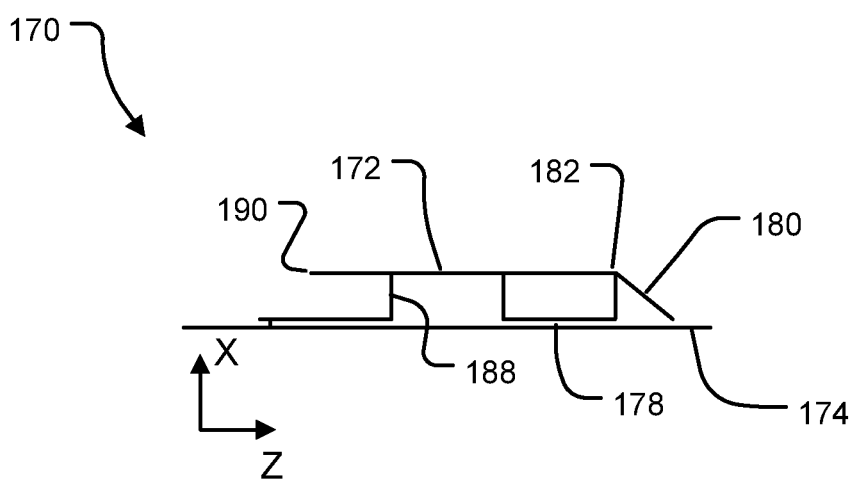
Figure 9B:
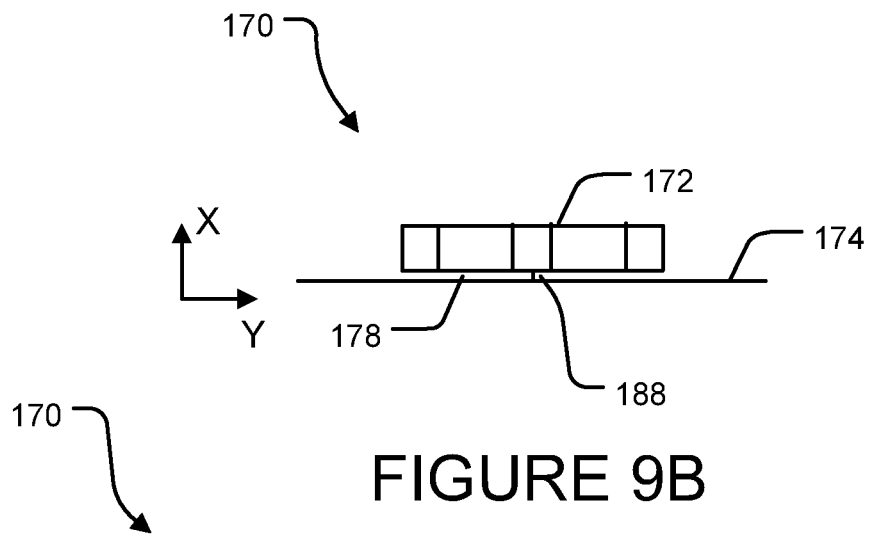
Figure 9C:
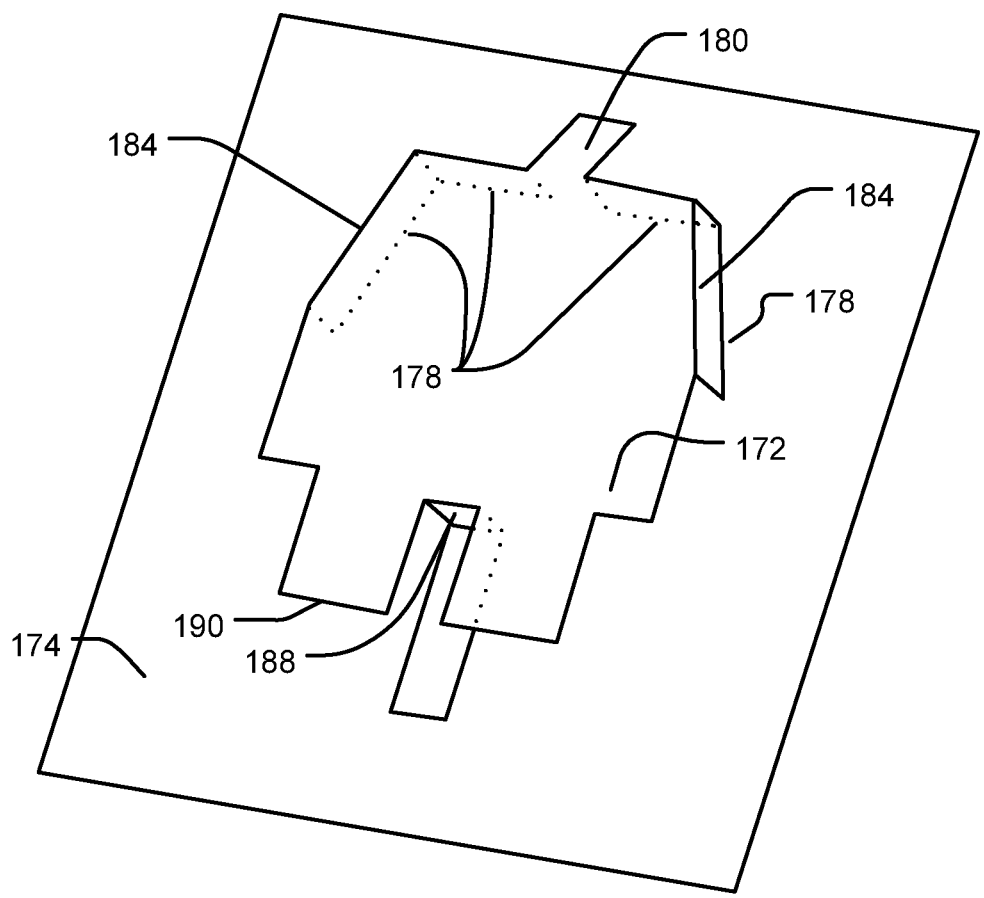

It can be appreciated that the invention has several aspects including:

antennas having features of antennas like those in FIGS. 8, 8A and 8B that may be applied for any purpose;

antennas having features of an antenna like the one shown in FIGS. 9, 9A and 9B that may be applied for any purpose;

monitoring systems that may be used for monitoring the presence, heart rate and/or respiration rate of one or more persons of which the system of FIG. 1 is an example;

monitoring systems that may be used to monitor the well being of an infant or single person—examples of such systems include baby monitors and systems for waking a person who suffers from sleep apnea if the person stops breathing for more than a short time; and, sensors based on UWB radar that may be used to monitor for the presence, heart rate and/or respiration rate of a person. Such sensors may be used, for example, by emergency personnel (e.g. firefighters, ambulance attendants, emergency response technicians, military medics or the like) to test for the presence of vital signs in injured or unwell people. Such sensors may be portable. In some embodiments the sensors are configured to be pressed against the back or chest of a person and include a display or other indicator that identifies whether or not vital signs (e.g. heat beat and/or breathing) can be detected and may provide information such as heart rate and breathing rate.

sensors based on UWB radar that may be used to detect a pulse at a location on an individual. Such sensors may be used, for example, in non-invasive blood pressure monitors which compute blood pressure of an individual based upon the speed of propagation of pulses in the individual's circulatory system. Such sensors may be provided, for example, at a person's neck and ankle. The difference in the time at which a pulse is detected at these two locations may be correlated to the individual's blood pressure. Two such sensors may be connected to a controller that determines a difference in time between the arrival of pulses at the sensors and computes a blood pressure or a change in a blood pressure based at least in part on that time difference.

Certain implementations of the invention comprise computer processors which execute software instructions which cause the processors to perform a method of the invention. For example, one or more processors in a sensing unit or a combination of processors in sensing units and a monitoring station may implement the methods for obtaining heart rate and breathing rate information that are described herein by executing software instructions in a program memory accessible to the processors. The invention may also be provided in the form of a program product. The program product may comprise any medium which carries a set of computer-readable signals comprising instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including, as equivalents of that component, any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

- In some embodiments transmit pulses are distributed among several transmit antennas such that the transmit antennas transmit UWB pulses in different time slots. In each of the time slots reflected pulses may be detected at a plurality of receive antennas. In some embodiments, this is achieved by distributing transmit signals to each of several antennas which are placed at various locations and are separated from the UWB transmitter by different RF path lengths.
- In some of the implementations described above, a switched amplifier is used for RF switch 82. However, a suitable RF switch can also be implemented using other technologies such as PIN diodes, Schottky Diodes, micro-electro-mechanical (MEM) switches and the like. Some embodiments which are designed for short range lack a switch 82.

Accordingly, the scope of the invention is to be construed in accordance with the substance defined by the following claims.

What is claimed is:

1. Apparatus for monitoring vital signs of one or more living subjects, the apparatus comprising:
   a monitoring station;
   at least one sensor in communication with the monitoring station, the sensor comprising:
     an antenna system;
     an ultra wideband radar system coupled to the antenna system;
     a signal processor connected to receive a signal from the ultra wideband radar system and configured to extract from the signal information about one or more vital signs of a living subject in a sensing volume corresponding to the antenna system; and
     a communication system configured to transmit the information to the monitoring station;
   wherein the antenna system comprises one or more groups of antennas and each group of antennas comprises: a transmit antenna connected to transmit ultra wideband pulses generated by the ultra wideband radar system; and a plurality of receive antennas spaced apart from the transmit antenna and connected to receive ultra wideband pulses reflected by the living subject; and
   wherein, for each group of antennas, the plurality of receive antennas have higher gains than the transmit antenna; and
   wherein the antenna system comprises a generally planar substrate and at least one antenna that comprises a first element on a first side of the substrate and a second element on a second side of the substrate opposed to the first side, wherein each of the first and second elements are symmetrical about a centre line.

2. Apparatus according to claim 1 wherein each of the elements comprises a plurality of stubs and wherein at least one of: the stubs are pointed; the stubs are of different lengths; and the stubs include a central stub having edges that follow intersecting straight lines.

3. Apparatus according to claim 1 comprising a mattress wherein the antenna system is located below an upper surface of the mattress.

4. Apparatus according to claim 3 wherein the antenna system comprises an array of antennas extending across the mattress in a band at a location between head and foot ends of the mattress.

5. Apparatus according to claim 1 wherein the radar system comprises a transmitter configured to generate transmitted pulses having durations of 3 ns or less and a receiver which is gated by pulses having lengths in excess of the lengths of the transmitted pulses.

6. Apparatus according to claim 1 wherein the signal processor comprises a data processor executing instructions that cause the data processor to transform the signal into the frequency domain and to identify a peak in the transformed signal lying within a band of frequencies characteristic of heart rates.

7. Apparatus according to claim 6 wherein the instructions cause the data processor to search for a peak in a frequency range that is based at least in part upon a previously-determined heart rate.

8. Apparatus according to claim 1 wherein the signal processor comprises a data processor executing instructions that cause the data processor to transform the signal into the frequency domain and to identify a peak lying within a band of frequencies characteristic of breathing rates.

9. Apparatus according to claim 1 wherein the signal processor is configured to detect motion artefacts in the signal and to generate a motion-sensed signal indicating that the living subject is moving; and wherein the monitoring station is configured to temporarily suppress display of updated information regarding a vital sign in response to receiving the motion-sensed signal from the signal processor.

10. Apparatus according to claim 1 wherein the radar system comprises first and second reflected power outputs that carry first and second reflected power signals and the signal processor is configured to monitor a difference between the first and second reflected power signals and to generate an occupancy signal based at least in part upon the difference.

11. Apparatus according to claim 1 wherein the monitoring station comprises a display and is configured to display on the display indicia indicating whether or not the sensor detects that the living subject is moving and wherein the apparatus comprises means for monitoring a motion signal indicative of motions of the living subject and, based at least in part upon an amplitude or duration of the motion signal, determining that the motions of the living subject are not normal and wherein the monitoring station is configured to display on the display indicia indicating that the motions of the living subject are not normal.

12. Apparatus according to claim 1 wherein the at least one sensor comprises a chair sensor, the chair sensor mounted on or built into a backrest of a chair.

13. Apparatus according to claim 1 wherein the ultra wideband radar system transmits pulses having frequencies less than about 12 GHz.

14. Apparatus according to claim 13 wherein the frequencies are in the range of about 3.6 GHz to about 4.6 GHz.

15. Apparatus according to claim 1 wherein the ultra wideband radar system transmits pulses with a pulse repetition interval in the range of about 0.5 μs to about 1 μs.

16. Apparatus according to claim 1 wherein, for each group of antennas, the plurality of receive antennas are approximately equally spaced apart from the transmit antenna.

17. Apparatus for monitoring vital signs of one or more living subjects, the apparatus comprising:
a monitoring station;
at least one sensor in communication with the monitoring station, the sensor comprising:
an antenna system;
an ultra wideband radar system coupled to the antenna system;
a signal processor connected to receive a signal from the ultra wideband radar system and configured to extract from the signal information about one or more vital signs of a living subject in a sensing volume corresponding to the antenna system; and
a communication system configured to transmit the information to the monitoring station;
wherein the antenna system comprises one or more groups of antennas and each group of antennas comprises: a transmit antenna connected to transmit ultra wideband pulses generated by the ultra wideband radar system; and a plurality of receive antennas spaced apart from the transmit antenna and connected to receive ultra wideband pulses reflected by the living subject; and
wherein, for each group of antennas, the plurality of receive antennas have higher gains than the transmit antenna; and
wherein the antenna system comprises a circuit board, a ground plane on the circuit board, and at least one antenna that comprises a three-dimensional radiating element mounted directly to the circuit board over the ground plane, wherein the radiating element comprises an open end and a stub extended over the open end.

18. Apparatus according to claim 17 comprising a mattress wherein the antenna system is located below an upper surface of the mattress.

19. Apparatus according to claim 18 wherein the antenna system comprises an array of antennas extending across the mattress in a band at a location between head and foot ends of the mattress.

20. Apparatus according to claim 17 wherein the radar system comprises a transmitter configured to generate transmitted pulses having durations of 3 ns or less and a receiver which is gated by pulses having lengths in excess of the lengths of the transmitted pulses.

21. Apparatus according to claim 17 wherein the signal processor comprises a data processor executing instructions that cause the data processor to transform the signal into the frequency domain and to identify a peak in the transformed signal lying within a band of frequencies characteristic of heart rates.

22. Apparatus according to claim 21 wherein the instructions cause the data processor to search for a peak in a frequency range that is based at least in part upon a previously-determined heart rate.

23. Apparatus according to claim 17 wherein the signal processor comprises a data processor executing instructions that cause the data processor to transform the signal into the frequency domain and to identify a peak lying within a band of frequencies characteristic of breathing rates.

24. Apparatus according to claim 17 wherein the signal processor is configured to detect motion artefacts in the signal and to generate a motion-sensed signal indicating that the living subject is moving; and wherein the monitoring station is configured to temporarily suppress display of updated information regarding a vital sign in response to receiving the motion-sensed signal from the signal processor.

25. Apparatus according to claim 17 wherein the radar system comprises first and second reflected power outputs that carry first and second reflected power signals and the signal processor is configured to monitor a difference between the first and second reflected power signals and to generate an occupancy signal based at least in part upon the difference.

26. Apparatus according to claim 17 wherein at least one of: the antenna comprises an input feed point recessed from an edge of the radiating element; the radiating element tapers in width toward the open end; and the radiating element comprises skirt portions that extend toward the ground plane along lateral edges of the radiating element.

27. Apparatus according to claim 17 wherein the monitoring station comprises a display and is configured to display on the display indicia indicating whether or not the sensor detects that the living subject is moving and wherein the apparatus comprises means for monitoring a motion signal indicative of motions of the living subject and, based at least in part upon an amplitude or duration of the motion signal, determining that the motions of the living subject are not normal and wherein the monitoring station is configured to display on the display indicia indicating that the motions of the living subject are not normal.

28. Apparatus according to claim 17 wherein the at least one sensor comprises a chair sensor, the chair sensor mounted on or built into a backrest of a chair.

29. Apparatus according to claim 17 wherein the ultra wideband radar system transmits pulses having frequencies less than about 12 GHz.

30. Apparatus according to claim 29 wherein the frequencies are in the range of about 3.6 GHz to about 4.6 GHz.

31. Apparatus according to claim 17 wherein the ultra wideband radar system transmits pulses with a pulse repetition interval in the range of about 0.5 μs to about 1 μs.

32. Apparatus according to claim 17 wherein, for each group of antennas, the plurality of receive antennas are approximately equally spaced apart from the transmit antenna.

* * * * *